United States Patent

Schonert et al.

(10) Patent No.: US 6,945,254 B2
(45) Date of Patent: Sep. 20, 2005

(54) METHOD FOR SIMULTANEOUSLY DYEING AND PERMANENT SHAPING OF HAIR

(75) Inventors: Dieter Schonert, Reinheim-Georgenhausen (DE); Anette Schmidt-Hoerr, Gr.-Bieberau (DE); Uwe Lenz, Zwingenberg (DE)

(73) Assignee: Wella Aktiengesellschaft, Darmstadt (DE)

( * ) Notice: Subject to any disclaimer, the term of this patent is extended or adjusted under 35 U.S.C. 154(b) by 287 days.

(21) Appl. No.: 10/198,548

(22) Filed: Jul. 18, 2002

(65) Prior Publication Data

US 2003/0084518 A1 May 8, 2003

(30) Foreign Application Priority Data

Sep. 4, 2001 (DE) ......................................... 101 43 293

(51) Int. Cl.$^7$ .................................................. A61K 7/08
(52) U.S. Cl. ....................... 132/202; 132/208; 132/210; 8/405; 8/406; 8/410; 8/421; 8/459; 8/587
(58) Field of Search ................................ 132/202, 208, 132/210; 8/405, 406, 410, 421, 459, 587, 408, 546, 588, 592

(56) References Cited

U.S. PATENT DOCUMENTS 4,566,875 A * 1/1986 Grollier et al. ............... 8/406

FOREIGN PATENT DOCUMENTS

| DE | 1 129 261 | 5/1962 |
| EP | 0 352 375 B1 | 11/1994 |
| GB | 876 663 | 9/1961 |

OTHER PUBLICATIONS

"Dauerwellen Und Haarfaerben in Einem Arbeitsgang" Kosmetik–Parfum–Drogen Rundschau 3/4 1965, pp. 35–36.

* cited by examiner

Primary Examiner—Margaret Einsmann
Assistant Examiner—Eisa Elhilo
(74) Attorney, Agent, or Firm—Michael J. Striker

(57) ABSTRACT

The method for simultaneously dyeing and permanent shaping of hair includes dividing the hair into strands an winding the strands onto curlers: mixing a hair shaping component (A) containing from 6 to 15 percent by weight of a keratin-reducing substance with a dye component (B) to form a dyeing and shaping composition prior to application on the hair; treating the hair with the dyeing and shaping composition and then allowing it to act on the hair for an acting time sufficient for the permanent shaping; after that, treating the hair with a fixing composition; allowing the fixing composition to act on the hair from 1 to 40 minutes and then subsequently rinsing the hair. The dye component (B) contains at least one oxidative coupler compound and at least one oxidative dyestuff selected from a group consisting of certain 4,5-diamino-pyrazole derivatives and certain aminophenol derivatives.

13 Claims, No Drawings

METHOD FOR SIMULTANEOUSLY DYEING AND PERMANENT SHAPING OF HAIR

BACKGROUND OF THE INVENTION

The subject matter of the present invention comprises a method for simultaneously permanent shaping of hair, especially of natural hair and dyed hair, and dyeing the hair and/or hair color renewing. In a first step of this method the hair swells and its natural pH is changed and at the same time the disulfide bridge bonds of the hair are opened and the dyestuffs for the hair are applied to the hair. In a second step the disulfide bridges are closed again by a reforming treatment and the dyestuffs on the hair are oxidatively developed.

The classical technique for performing the permanent hair shaping consists in that in a first step the disulfide bonds of the hair keratin are opened with the help of an agent, which contains an effective reducing ingredient, and subsequently the disulfide bonds are again reformed using a fixing composition containing an oxidizing agent. Suitable reducing agents include sulfites, thioglycolic acid, thiolactic acid, 3-mercaptopropionic acid, mercaptocarboxylic acid esters and cysteine. These reducing agents are either acidic (sulfite, bisulfite and mercaptocarboxylic acid esters) or alkaline (alkali and ammonium salts of mercaptocarboxylic acids). In the case of alkali-adjusted shaping agents the required alkalinity is obtained, above all, by addition of ammonia, organic amines, ammonium or alkali carbonates and ammonium or alkali hydrogen carbonate. Especially hydrogen peroxide-containing or bromate-containing liquids can be used as the fixing agent.

Permanent shaping of human hair generally takes place, when the washed and hand towel dried hair is first divided into several parts and these parts are then wound on curlers.

After finishing winding the hair on the curlers the curlers are thoroughly moistened with the required amount of permanent shaping composition. The curlers used for the permanent shaping have a diameter of about 5 to 13 millimeters, while curlers for hair curling have a diameter of over 13 millimeters.

The acting time of the permanent shaping composition during a permanent treatment depends on the desired degree of reforming of the disulfide bonds and the condition of the hair, and amounts to about 3 to 30 minutes. Heating the hair, for example using a radiant heater or a drying hood, may shorten the acting time.

After expiration of the required acting time of the permanent shaping composition, the hair is rinsed with water and treated with a fixing agent, for example an aqueous solution of hydrogen peroxide or potassium bromate. The acting time of the fixing composition usually amounts to about 1 to 30 minutes. Subsequently the curlers are removed, if necessary the hair is still after-treated with the fixing agent for a few minutes and then rinsed with water, put in a hairstyle and dried.

Frequently however dyeing or tinting the hair is desired as well as a permanent shaping of the hair. Especially the hair looses a large part of its color and its luster during a permanent wave treatment. A special dyeing process is then required after the permanent shaping of the hair. However in the case of an oxidative dyeing this leads to excessive stress of the hair, since each oxidative dyeing of the hair or permanent shaping treatment acts aggressively on the hair structure. Dyeing or tinting is not uniform over the entire hair length according to the differences in hair structure. The permanence of the dyeing is only guaranteed for a short time, since after a few hair washings the dye is washed out from the hair. This leads to a lengthening of the entire treatment process.

A reduction in the structural stress on the hair and an improvement of the permanence of the hair dyeing can be achieved by simultaneously performing the hair shaping and dyeing treatment. A combination of both treatments of this type would also save time.

There have already been many attempts to provide methods for simultaneously performing permanent shaping of hair and dyeing of hair. For example, such methods are disclosed in DE-AS 1 129 261 and GB-PS 876 663. These prior art methods permit simultaneous permanent shaping and dyeing of hair, including white and gray hair. These methods are based on a permanent shaping composition, which comprises an aqueous solution of a keratin-reducing agent and a suitable basic dye precursor compound. The dye precursor compound is in the form of a stable leuko-compound, for example Crystal violet, Methylene blue, Fuchsine or Malachite green, and is converted with a subsequently applied oxidative fixing agent to the actual dyestuff that acts on the hair.

The possibility of simultaneously dyeing and permanent shaping of the hair by addition of oxidation dye precursor compounds to an alkaline thioglycolate solution is discussed in the review article "Permanent Shaping and Hair Dyeing in One Working Process {Dauerwellen und Haarfärben in einem Arbeitsgang}", by R. Heilingötter, in Cosmetic-Perfume-Drugs Review {Kosmetik-Parfüm-Drogen Rundschau} ¾ (1965), pp. 35–36. Finally a method for permanent shaping and simultaneously dyeing of hair is described in EP-B 0 352 375. In this latter method the hair is first treated with a first composition. This first composition contains from 0.1 to 6 percent by weight of thioglycolate and 3 to 10 percent by weight of cysteine as keratin-reducing agent, from 0.01 to 4 percent by weight of para-phenylenediamine and/or ortho-phenylenediamine and from 0.01 to 1 percent by weight of resorcinol as oxidation dye precursor compounds. The first composition also contains from 0.01 to 1 percent by weight of antioxidant, from 0.01 to 1 percent by weight heavy metal complexing agent, from 0.01 to 1 percent by weight surfactant and an alkalizing agent for adjustment of the pH to from 9.0 to 9.5. After that a second composition containing from 3 to 8 percent by weight of hydrogen peroxide is applied to the hair without rinsing the previous first composition from the hair.

However all currently known methods for permanent shaping of hair and simultaneous dyeing or tinting of hair have the disadvantage that the results obtained are not always satisfactory. Several of the dyestuffs, for example certain oxidation hair dye compounds, which are employed in these methods, are unstable in the strongly reducing thioglycolate solution. They react reductively during extended storage and their dyeing power is lost so that the making of commercial preparations is impossible. Also the red shades of special interest are not satisfactorily obtained with these dye compounds. Other dyestuffs used in methods of simultaneously dyeing and permanent shaping, for example the dyestuffs described in DE-AS 1 129 261 and GB-PS 876 663, provide dyed hair colors with only an insufficient light fastness.

Conventional permanent shaping methods especially cause a significant color loss, especially for dyed hair. Permanently waved natural hair notably looses its luster and is partially bleached by the treatment. Because of that the hair colors are dull and feeble.

SUMMARY OF THE INVENTION

It is an object of the present invention to provide a process for simultaneously permanently shaping and dyeing human hair, especially natural hair, better, faster and more carefully than the processes of the prior art.

It is another object of the present invention to provide a process for simultaneously permanently shaping and dyeing human hair, which preserves and/or renews the color intensity of dyed hair and improves its luster during permanent shaping.

According to the invention the method for simultaneously dyeing and/or refresh dyeing and permanent shaping of hair comprises the steps of:

a) immediately prior to application on the hair, mixing a hair shaping component (A) containing from 6 to 15 percent by weight of a keratin-reducing substance with a dye component (B) to form a dyeing and shaping composition;

b) treating the hair with the dyeing and shaping composition;

c) then allowing the dyeing and shaping composition to act on the hair for from 3 to 30 minutes;

d) after the allowing of step c), treating the hair with a fixing composition;

e) then allowing the fixing composition to act on the hair from 1 to 40 minutes; and f) rinsing the hair;

wherein the dye component (B) contains at least one oxidative coupler compound and at least one oxidative dyestuff as oxidation dye precursor. compounds, said at least one oxidative dyestuff is selected from the group consisting of 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 4,5-diamino-1-[(4-chlorophenyl)methyl]-1H-pyrazole, 4,5-diamino-1-methyl-pyrazole, 2-amino-6-methylphenol, 2-amino-5-methyl phenol and p-aminophenol derivatives of formula (I):

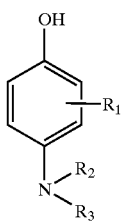

(I)

wherein $R_1$ represents H, —$CH_3$, —$CH_2CH_3$, —$CH_2OH$, —$CH_2CH_2OH$, —$CH_2NH_2$, —$CH_2NHCH_2CH_2OH$ or —$CH_2OCH_3$ and $R_2$ and $R_3$, independently of each other, each represent H, —$CH_3$, —$CH_2CH_3$, —$CH_2OH$, —$CH_2CH_2OH$ or —$CH_2CH_2CH_2OH$, with the proviso that at least one of the groups $R_1$, $R_2$ and $R_3$ is not H.

Preferably the at least one oxidative dyestuff is selected from the group consisting of 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 4,5-diamino-1-[(4-chlorophenyl)methyl]-1H-pyrazole, 4,5-diamino-1-methyl-pyrazole, 2-amino-6-methylphenol, 2-amino-5-methyl phenol, 4-amino-3-methyl-phenol, 4-methylaminophenol, 4-amino-2-(aminomethyl)phenol, 4-amino-2-[(2-hydroxyethyl)amino]methylphenol and 4-amino-2-(methyoxymethyl)phenol. The 4-5-diaminopyrazole derivatives are especially preferred.

The at least one oxidative coupler compound is preferably selected from the group consisting of 1,3-diaminobenzene, 2-amino-4-[(2-hydroxyethyl)amino]-anisole, 2,4-diamino-1-fluoro-5-methylbenzene, 2,4-diamino-1-methoxy-5-methyl-benzene, 2,4-diamino-1-ethoxy-5-methylbenzene, 2,4-diamino-1-(2-hydroxy-ethoxy)-5-methylbenzene, 2,4-di[(2-hydroxyethyl)amino]-1,5-dimethoxybenzene, 2,4-diamino-1-(2-hydroxyethoxy)benzene, 3-di[(2-hydroxyethyl)amino]aniline, 3-di[(2-aminoethyl)amino]aniline, 4-amino-1-ethoxy-2-di[(2-hydroxyethyl)-amino]-benzene, 3-[(2-hydroxyethyl)-amino]aniline, 1,3-di(2,4-diaminophenoxy)propane, 2,4-dimethoxy-1,3-diaminobenzene, 2,6-bis(2-hydroxyethylaminotoluene, 3-dimethylaminophenol, 5-amino-2-methylphenol, 5-amino-4-fluoro-2-methyl-phenol, 5-amino-4-methoxy-2-methylphenol, 5-amino-4-ethoxy-2-methylphenol, 3-amino-2,4-dichlorophenol, 3-dimethylaminophenol, 3-amino-2-chloro-6-methyl-phenol, 3-aminophenol, 3-[(amidomethyl)amino]phenol, 5-[(2-hydroxyethyl)-amino]-2-methylphenol, 3-[(2-hydroxyethyl)amino]phenol, 5-amino-2-ethylphenol, 5-[(3-hydroxy-propyl)amino]-2-methylphenol, 3-[(2,3-dihydroxypropyl)amino]-2-methylphenol, 3-[(2-hydroxyethyl)amino]-2-methylphenol, 5-amino-4-chloro-2-methylphenol, methylenedioxyphenol, resorcinol, methylresorcinol and 4-chlororesorcinol.

The dye component preferably also includes oxidation dye precursor compounds selected from the group consisting of 1,4-diaminobenzene, 1,4-diamino-2-methylbenzene, 1,4-diamino-2,6-dimethylbenzene, 1,4-diamino-2,5-dimethylbenzene, 1,4-diamino-2,3-dimethylbenzene, 1,4-diamino-2-chloro-benzene, 4-di[(2-hydroxyethyl)amino]aniline, 4-[(2-methoxyethyl)amino]aniline, 1,4-diamino-2-(2-hydroxyethyl)benzene, 1,3-bis[N-(2-hydroxyethyl)-N-(4-amino-phenyl)]amino-2-propanol and 2',2-[1,2-ethandiyl-bis(oxy-2,1-ethandiyloxy)]bis-1,4-diaminobenzene.

The dye component (B) also can include direct-dyeing dye compounds selected from the following groups of direct dyes.

Nitro Dye Compounds (Blue)

4-N-ethyl-N-(2'-hydroxyethyl)amino-1-(2"-hydroxyethyl)amino-2-nitrobenzene, 1-amino-3-methyl-4-(2'-hydroxyethyl)amino-5-nitrobenzene, 1-(2'-hydroxyethyl)amino-2-nitro-4-bis-(2"-hydroxyethyl)aminobenzene, 4-bis-(2'-hydroxy-ethyl)amino-1-(2"-methoxyethyl)aminonitrobenzene, 1-(2',3'-dihydroxypropyl)-amino-2-nitro-4-[ethyl-(2"-hydroxyethyl)amino]benzene, 1-[(2',3'-dihydroxy-propyl)amino]-2-nitro-4-[ethyl-2"-(hydroxyethyl)amino]benzene and 1-(3'-hydroxypropylamino)-2-nitro-4-bis-(2"-hydroxyethylamino)benzene.

Nitro Dye Compounds (Red)

1-amino-4-(2'-hydroxyethyl)aminonitrobenzene, 1-hydroxy-2-amino-4,6-dinitro-benzene, 1-amino-2-nitro-4-bis-(2'-hydroxyethyl)aminobenzene, 1-amino-2-nitro-4-(2'-hydroxyethyl)amino-5-chlorobenzene, 1-(2'-hydroxyethyl)amino-2-nitro-4-aminobenzene, 1-hydroxy-3-nitro-4-aminobenzene, 1-(2'-aminoethyl)-amino-2-nitro-4-(2"-hydroxyethyl)oxybenzene, 3-nitro-4-(2'-hydroxyethyl)aminophenyl glyceryl ether, 1-amino-5-chloro-4-(2',3'-dihydroxypropyl)amino-2-nitrobenzene, 1,4-bis-[(2',3'-dihydroxypropyl)amino]-5-chloro-2-nitrobenzene, 1-hydroxy-2-(2'-hydroxyethyl)amino-4,6-dinitrobenzene, 2-amino-6-chloro-4-nitrophenol, 1-hydroxy-3-nitro-4-(3'-hydroxypropylamino)benzene, 3-nitro-4-ethylaminobenzoic acid, 4-amino-2-nitrodiphenylamino-2-carboxylic acid, 2-chloro-6-ethylamino-4-nitrophenol, 2,5-diamino-6-nitropyridine and 1,2,3,4-tetrahydro-6-nitroquinoxaline.

Nitro Dye Compounds (Yellow)

4-(2'-hydroxyethyl)amino-3-nitrobenzonitrile, 4-(2'-hydroxyethyl)amino-3-nitro-benzamide, 1-amino-2-(2'-hydroxyethyl)amhno-5-nitrobenzene, 1-methoxy-2-(2'-hydroxyethyl)amino-5-nitrobenzene, 1-hydroxy-3-nitro-4-(2'-hydroxyethyl)-aminobenzene, 1-hydroxy-2-amino-3-nitrobenzene, 1-amino-2-methyl-6-nitro-benzene, 1-(2'-hydroxyethyl)-oxy-3-methylamino-4-nitrobenzene, 1-methylamino-2-nitro-5-(2',3'-dihydroxypropyl)oxybenzene, 1-(2'-hydroxyethyl)-amino-2-hydroxy-4-nitrobenzene, 1-methoxy-3-(2'-aminoethyl)amino-4-nitrobenzene, 4-(2'-ureidoethyl)-amino-4-nitrobenzene, 1-(2'-hydroxyethyl)amino-2-nitro-benzene, 4-(2'-hydroxyethyl)amino-3-nitrotrifluoromethylbenzene, 2,4-bis-[N-(2'-hydroxyethyl)amino]-5-chloronitrobenzene, 4-(2',3'-dihydroxypropyl)-amino-3-nitro-trifluoromethylbenzene, 4-(2'-hydroxymethyl)amino-3-nitro-methylbenzene and 4-(2'-hydroxyethyl)amino-3-nitrochlorobenzene.

Azo Dye Compounds 1-(4'-nitrophenylazo)-2-methyl-4-bis-(2"-hydroxyethyl)aminobenzene, 1-(3'-nitro-4-amino)phenazo-2-hydroxy-7-trimethylammonium chloride naphthalene, 1-(2'-hydroxy-4'-sulfo-6'-nitro)naphthylazo-2-hydroxynaphthalene, 1-(4'-amino-phenyl-azo)-2-methyl-4-bis-[(2'-hydroxyethyl)amino]benzene, 5-(4'-dimethyl-amino-phenylazo)-1,4-dimethyltriazonium chloride, 1'-(2'-methoxyphenylazo)-2-hydroxy-7-trimethylammonium naphthalene chloride, 1-(4'-aminophenylazo)-2-hydroxy-7-trimethylammonium naphthalene, 4-(3'-trimethylammoniumphenyl-azo)-N-phenyl-3-methylpyrazolone (5), 4-hydroxy-3-[(4'-sulfo-1'-naphthayl-azo]-1-naphthalene sulfonic acid, 1-(4'-sulfophenylazo)-2-hydroxynaphthalene, 1-(4'-sulfophenylazo)-2-hydroxy-6-sulfonaphthalene, 4-amino-[4'-bis-(2"-hydroxyethyl)aminoazo-benzene, 4-amino-[4'-bis-(2"-hydroxyethyl)amino]-2'-methylazobenzene, 3-(2',6'-diaminopyridyl-3'-azo)pyridine, 7-phenylazo-1-amino-3,6-disulfo-8-hydroxynaphthalene, 5-acetylamino-4-hydroxy-3-[(2'-methylphenyl)azo]-2,7-naphthalene disulfonic acid, 2-(2',4'-dimethyl-phenylazo)-6-(4"-sulfophenylazo)-1,3-dihydroxybenzene.

Quinone Dye Compounds 1,4-bis-(2',3'-dihydroxypropyl)aminoanthraquinone, 1-methylamino-4-(2'-hydroxyethyl)aminoanthraquinone, 2-(2'-aminoethyl)aminoanthraquinone, 2-bromo-4,8-diamino-6-(3'-trimethylammonium)phenylamino-1,5-naphthoquinone, 1-(2'-sulfo-4'-methylphenyl)amino-4-hydroxyanthrquinone, 1,4-diaminoanthraquinone, 1-amino-2-sulfo-4-cylcohexylaminoanthraquinone, 1-methylamino-4-aminoppropylaminoanthraquinone, 1-aminopropyl-aminoanthraquinone.

Triphenylmethane Dye Compounds

4', 4",4'''-triamino-3-methyltriphenycarbonium chloride, bis-(4,4-diethyl-aminophenyl)-4'-ethylaminonaphthylcarbonium chloride, bis-(4,4-dimethyl-aminophenyl)-4'-phenylaminonaphthylcarbonium chloride and 4,4-bis-(N-ethyl-3-sulfobenzyl)-amino-2"-sulfofuchsonium.

Also natural dye compounds, such as henna, indigo and juglone, are suitable.

The dye component (B) preferably contains from 0.5 to 30 percent by weight, especially preferably from 1 to 10 percent by weight, of the dye compounds.

Preferably the dye component (B) similarly contains a hair keratin-reducing substance. The amount of hair keratin-reducing substance in the dye component (B) and in the dyeing and shaping composition is preferably from 2 to 20 percent by weight, especially preferably from 5 to 20 percent by weight.

The dye compounds are contained in the dyeing and shaping composition in an amount of 0.1 to 5 percent by weight, especially preferably from 0.5 to 3 percent by weight.

The dyeing and shaping composition is obtained by mixing the hair shaping component (A) and the dye component (B) with each other in a ratio of 1:1 to 10:1.

In an especially preferred embodiment of the method according to the invention the hair is treated with a fixing composition without rinsing the shaping agent from the hair first.

In another preferred embodiment of the inventive method an intervening rinse having a pH of 2 to 6 is applied to the hair after the acting time for the dyeing and shaping composition has expired and prior to treatment with the fixing composition.

In a further preferred embodiment of the inventive method the hair is treated with an acidic pre-fixing composition containing from 1 to 4 percent by weight of hydrogen peroxide after the acting time for the dyeing and shaping composition has expired and prior to treatment with the fixing composition.

The advantages of the present invention include improved permanence or stability in comparison to color renewal methods by means of a tinting agent and in improved hair care in comparison to hair shaping and dyeing in a two-step process. Furthermore the luster of the hair visibly increases. An intense dyed hair color results when the fixing composition is applied directly to the hair, without previously rinsing out the permanent wave liquid. The entire course of treatment is significantly more protective for the hair than the normal course of treatment during a permanent hair shaping.

In the method according to the invention the hair is washed, rubbed with a hand towel, pre-moistened with a portion of the dyeing and shaping composition, as needed, divided into individual strands and wound on curlers. Subsequently an amount of the dyeing and shaping composition sufficient for hair shaping is applied to the hair, generally about 80 g for average length hair.

The shaping agents employed in the method described here are based on conventional hair keratin-reducing substances, such as salts of sulfurous acid or certain mercapto compounds, especially salts or esters of mercaptocarboxylic acids. The hair-shaping component (A) contains the keratin-reducing compounds in the usual amount for hair shaping, for example the ammonium salts of thioglycolic acid, thiolactic acid or cysteine, in a concentration of 6 to 12 percent by weight. The pH value of the alkaline shaping composition is generally from 7 to 10. The pH is adjusted preferably with ammonia, monoethanolamine, ammonium carbonate or ammonium hydrogen carbonate.

If the shaping component (A) is to be adjusted so that it is acidic (e.g. at pH=6.5 to 6.9), esters of mercaptocarboxylic acid, such as monothioglycolic acid glycol ester or glycerol ester, preferably however mercaptoacetamide or 2-mercaptoproprionic acid amide, are employed in a concentration of 2 to 14 percent by weight; or however the salts of sulfurous acid, for example sodium, ammonium or monoethanol ammonium sulfite, are employed in a concentration of 3 to 8 percent by weight (calculated as $SO_2$).

Preferably the hair keratin-reducing compound employed is a salt or a derivative of a mercaptocarboxylic acid. A keratin-reducing compound selected from the group consisting of thioglycolic acid, cysteine, thiolactic acid and their salts is particularly preferred.

A swelling and penetrating agent can be added to the permanent hair-shaping component (A) to increase its effectiveness. This swelling and penetrating agent can be urea, multivalent alcohols, ether, melamine, alkali or ammonium thiocyanate, isopropanol, imidazolidin-2-one, 2-pyrrolidone and 1-methyl-2-pyrrolidone. The permanent hair-shaping component (A) contains from about 0.5 to 50 percent by weight of the swelling and penetrating agent, preferably from 2 to 30 percent by weight.

After an acting time sufficient for permanent shaping of hair, which depends on hair condition, pH and shaping effectiveness of the dyeing and shaping composition as well as on the application temperature, amounting to from 3 to 30 minutes, preferably 2 to 20 minutes, the hair is oxidatively fixed, preferably first without rinsing the shaping agent from the hair.

The fixing composition is applied to the hair in an amount of from 50 to 200 g, according to the abundance of the hair. Any oxidizing agent currently used in hair fixing compositions can be used in the fixing agent for the hair fixing. For example, potassium bromate, sodium bromate, sodium perborate, dehydro-ascorbic acid, hydrogen peroxide and urea peroxide can be used as the oxidizing agent. The concentration of the oxidizing agent differs according to the application time, usually from 1 to 40 minutes, preferably 5 to 20 minutes, and the application temperature, namely 25 to 50° C. Usually the oxidizing agent is used in a concentration of about 0.5 to 12.0 percent by weight in the fixing composition. The fixing composition can understandably contain other substances, for example weak acids or peroxide stabilizers.

Both the dyeing and shaping composition and the fixing composition can be in the form of an aqueous solution or an emulsion and in thickened form on an aqueous basis, especially as a cream, gel or paste.

A fixing composition in viscose form with a sufficiently thick consistency so that the hair of a sitting customer can be fixed is particularly preferred. In that case the hair of the customer does not need to be fixed in a washbasin, as in the conventional or prior art fixing method. Optimum dyed hair color is provided with a preferred direct application of the fixing composition without an intervening rinse. It is preferable that the fixing composition is an oxidizing agent-containing viscose preparation with a viscosity of 100 to 10,000 mPa·s at 25° C. Fixing compositions with a viscosity of 300 to 1000 mPa·s at 25° C. are especially preferred. The viscosity data was obtained by measurement with a Haake rotary viscometer Type VT 501 with a shear rate of 64.5 per s.

Similarly it is also possible to fill this agent under pressure in an aerosol can and to dispense it as aerosol foam from the can.

Understandably the fixing composition and also the dyeing and shaping composition can contain all those known and conventional additive ingredients used in this type of composition. For example, these compositions can contain thickeners, such as kaolin, bentonite, fatty acids, higher fatty alcohols, starches, polyacrylic acids, cellulose derivatives, alginates, petrolatum (Vaseline®) or paraffin oil; wetting agents or emulsifiers selected from the classes of anionic, cationic, amphoteric or nonionic surface-active substances, for example fatty alcohol sulfates, fatty alcohol ether sulfates, alkyl sulfonates, alkyl benzene sulfates, quaternary ammonium salts, alkyl betaines, ethoxylated fatty alcohols, ethoxylated alkyl phenols, fatty acid alkanol amides or ethoxylated fatty acid esters; turbidity-inducing agents, for example polyethylene glycol esters or alcohols, such as ethanol, propanol, isopropanol or glycerol; solvating agents, stabilizers, buffer substances, perfume oils, hair conditioning agents and hair care ingredients, such as lanolin derivative compounds, cholesterol, pantothenic acids, creatin or betaine. The compositions of the invention can also contain optical whitening agents in the form of cumarin, stilbene, napththalimide, benzoxazole or styryl derivatives. The above-mentioned additive ingredients are used in amounts usual for their purposes, for example the wetting agents and emulsifiers are employed in a concentration of about 0.2 to 30 percent by weight, based on the total amount of the preparation or composition. The thickeners are contained in an amount of about 0.1 to 25 percent, based on the total amount of the preparation or composition.

Subsequently the curlers are removed, the fixing composition is rinsed from the hair with water and the hair is treated further in the usual manner. Preferably the hair is put in a water wave in connection with the simultaneous dyeing and hair shaping.

The hair permanently shaped in this way has a longer lasting dyed color or renewed color (color refreshing) than provided by conventional tinting or dyeing methods. The method according to the invention provides the advantage that hair shaping and hair dyeing or dye color refreshing or renewal and improved luster are provided in a single working method. A careful and time-saving treatment of the hair is possible using the dyeing and shaping composition. The longer permanence or stability of the dyed hair color in comparison to conventional tinting methods that are used after a permanent shaping treatment is an additional advantage.

EXAMPLES

Example 1

Undamaged hair is washed with a shampoo, rubbed and wound on curlers with a diameter of 8 millimeters. Prior to application 40 g of the following shaping component A and 40 g of the following dye component B are mixed to form 80 g of the dyeing and shaping composition.

| | Component A |
|---|---|
| 16.0 g | ammonium thioglycolate, 70% aqueous solution |
| 1.0 g | ammonia, 25% aqueous solution |
| 4.0 g | ammonium hydrogen carbonate |
| 1.0 g | castor oil ethoxylated with 35 mol ethylene oxide |
| 0.5 g | perfume oil |
| to 100 g | water |
| | Component B |
| 10.00 g | ammonium thioglycolate, 70% aqueous solution |
| 1.00 g | castor oil ethoxylated with 35 mol ethylene oxide |
| 0.20 g | sodium sulfite |
| 0.10 g | perfume oil |
| 0.10 g | 3-aminophenol |
| 0.04 g | amino-4-[(2-hydroxyethyl)amino]anisole |
| 0.60 g | resorcinol |
| 0.40 g | p-toluylenediamine sulfate |
| 0.03 g | 2-amino-5-methylphenol |
| 0.50 g | 4-amino-3-methylphenol |
| 2.00 g | ethanol |
| to 100 g | water |

Both components have a pH value of 8.0, as does their mixture. Subsequently the dyeing and shaping composition is distributed uniformly on the hair that was wound on the curlers. The dyeing and shaping composition is allowed to act on the hair for an acting time of 20 min under an infrared radiator hood at a temperature of 40° C. Then the hair wound on the curlers is treated with 80 g of the following fixing composition.

| Liquid Fixing Composition | |
|---|---|
| 4.00 g | hydrogen peroxide, 50% aqueous solution |
| 0.10 g | salicylic acid |
| 0.20 g | disodium hydrogen phosphate |
| 0.15 g | o-phosphoric acid |
| 1.00 g | castor oil ethoxylated with 35 mol ethylene oxide |
| 0.10 g | vinyl pyrrolidone/styrene mixed polymerizate |
| 0.10 g | perfume oil |
| to 100 g | water |

The acting time for the fixing composition is 15 minutes. After expiration of the acting time the curlers are unwound and the hair is rinsed with warm water. The hair is dyed a dark gold-blond and has beautiful lustrous locks. Finally the customary styling of the hair with comb and brush follows.

Example 2

Oxidatively damaged and permanent waved hair is washed with a shampoo, rubbed and wound on curlers with a diameter of 8 millimeters. Prior to application 40 g of the shaping component A and 40 g of the following dye component B are mixed to form 80 g of the dyeing and shaping composition.

| Component A | |
|---|---|
| 10.0 g | ammonium thioglycolate, 70% aqueous solution |
| 0.5 g | ammonia, 25% aqueous solution |
| 2.0 g | ammonium hydrogen carbonate |
| 1.0 g | castor oil ethoxylated with 35 mol ethylene oxide |
| 0.5 g | perfume oil |
| 2.0 g | polydimethyldiallyl ammonium chloride homopolymer (CFTA: POLYQUATERNIUM-6) |
| to 100 g | water |

| Component B | |
|---|---|
| 13.00 g | ammonium thioglycolate, 70% aqueous solution |
| 1.00 g | coconut fatty alcohol ethoxylated with 10 mol ethylene oxide |
| 0.04 g | 1,3-diamino-4-(2-hydroxyethoxy)benzene sulfate |
| 2.00 g | resorcinol |
| 0.30 g | p-toluylenediamine sulfate |
| 0.80 g | 4-amino-2-hydroxytoluene |
| 1.30 g | 4,5-diamino-1-(2-hydroxyethyl)-1H-pyrazole sulfate |
| 0.10 g | perfume oil |
| 3.00 g | isopropanol |
| to 100 g | water |

Both components A and B have a pH value of 8.0. Subsequently the dyeing and shaping composition is distributed uniformly on hair wound on curlers. The dyeing and shaping composition is allowed to act on the hair for an acting time of 10 min under an infrared radiator hood at a temperature of 40° C. Then the hair wound on the curlers is treated with 80 g of the following fixing composition.

| Viscous Fixing Composition | |
|---|---|
| 4.00 g | hydrogen peroxide, 50% aqueous solution |
| 0.50 g | sodium lauryl sulfate |
| 1.00 g | disodium hydrogen phosphate |
| 4.00 g | cetyl stearyl alcohol |
| 0.10 g | salicylic acid |
| 0.30 g | perfume oil |
| to 100 g | water |

The acting time for the fixing composition is 5 minutes. After expiration of this acting time the curlers are unwound and the hair is treated with the viscous fixing composition for an additional 15 minutes. Subsequently the hair is rinsed with warm water. The hair is dyed an intense copper-red and has beautiful lustrous locks. Finally the customary styling of the hair with comb and brush follows.

Example 3

Oxidatively damaged and permanent waved hair is washed with a shampoo, rubbed and wound on curlers with a diameter of 8 millimeters. Prior to application 50 g of the following shaping component A and 30 g of the following dye component B are mixed to form 80 g of the dyeing and shaping composition.

| Component A | |
|---|---|
| 10.0 g | ammonium thioglycolate, 70% aqueous solution |
| 0.5 g | ammonia, 25% aqueous solution |
| 2.0 g | ammonium hydrogen carbonate |
| 1.0 g | castor oil ethoxylated with 35 mol ethylene oxide |
| 0.5 g | perfume oil |
| 2.0 g | polydimethyldiallyl ammonium chloride homopolymer (CFTA: POLYQUATERNIUM-6) |
| to 100 g | water |

| Component B | |
|---|---|
| 13.00 g | ammonium thioglycolate, 70% aqueous solution |
| 1.00 g | castor oil ethoxylated with 35 mol ethylene oxide |
| 0.10 g | 3-aminophenol |
| 0.55 g | 2-methylresorcinol |
| 0.05 g | alpha-naphthol |
| 1.70 g | p-toluylenediamine sulfate |
| 0.01 g | N,N-bis(2-hydroxyethyl)-p-phenylenediamine monosulfate |
| 0.10 g | perfume oil |
| 2.00 g | ethanol |
| to 100 g | water |

Both components A and B have a pH value of 8.0. Subsequently the dyeing and shaping composition is distributed uniformly on hair wound on curlers.

The dyeing and shaping composition is allowed to act on the hair for an acting time of 10 min under an infrared radiator hood at a temperature of 40° C. Then the hair wound on the curlers is treated with 100 g of the following acidic intervening rinse, having a pH of 2.5 and the intervening rinse is allowed to act for five minutes.

| Acidic Intervening Rinse | |
|---|---|
| 2.00 g | cetyltrimethyl ammonium chloride |
| 8.00 g | citric acid |
| 10.00 g | lactic acid, 90% |
| 5.00 g | glyoxylic acid |
| to 100 g | water |

Subsequently the hair is treated with the following liquid fixing composition.

| Liquid Fixing Composition | |
|---|---|
| 4.00 g | hydrogen peroxide, 50% aqueous solution |
| 0.10 g | salicylic acid |
| 0.15 g | o-phosphoric acid |
| 1.00 g | castor oil ethoxylated with 35 mol ethylene oxide |
| 0.10 g | vinyl pyrrolidone/styrene mixed polymerizate |
| 0.10 g | perfume oil |
| to 100 g | water |

The acting time for the fixing composition is 15 minutes. After expiration of the acting time the curlers are unwound and the hair is rinsed with warm water. The hair has beautiful lustrous locks, which are dyed a warm brown shade. Finally the customary styling of the hair with comb and brush follows.

Example 4

Oxidatively damaged and permanent waved hair is washed with a shampoo, rubbed and wound on curlers with a diameter of 8 millimeters. Prior to application 50 g of the following shaping component A and 30 g of the following dye component B are mixed to form 80 g of the dyeing and shaping composition.

| Component A | |
|---|---|
| 10.0 g | ammonium thioglycolate, 70% aqueous solution |
| 0.5 g | ammonia, 25% aqueous solution |
| 2.0 g | ammonium hydrogen carbonate |
| 1.0 g | castor oil ethoxylated with 35 mol ethylene oxide |
| 0.5 g | perfume oil |
| 2.0 g | polydimethyldiallyl ammonium chloride homopolymer (CFTA: POLYQUATERNIUM-6) |
| to 100 g | water |

| Component B | |
|---|---|
| 13.00 g | ammonium thioglycolate, 70% aqueous solution |
| 1.00 g | castor oil ethoxylated with 35 mol ethylene oxide |
| 0.10 g | 3-aminophenol |
| 0.55 g | 2-methylresorcinol |
| 0.05 g | alpha-naphthol |
| 1.70 g | p-toluylenediamine sulfate |
| 0.01 g | N,N-bis(2-hydroxyethyl)-p-phenylenediamine monosulfate |
| 0.10 g | perfume oil |
| 2.00 g | ethanol |
| to 100 g | water |

Both components A and B have a pH value of 8.0. Subsequently the dyeing and shaping composition is distributed uniformly on hair wound on curlers.

The dyeing and shaping composition is allowed to act on the hair for an acting time of 10 min under an infrared radiator hood at a temperature of 40° C. Then the hair wound on the curlers is treated with 100 g of the following acidic pre-fixing composition, which is allowed to act on the hair for five minutes.

| Acidic Pre-fixing Composition | |
|---|---|
| 4.00 g | hydrogen peroxide, 50% aqueous solution |
| 0.10 g | salicylic acid |
| 1.00 g | copolymer of the semiester of itaconic acid, stearyl alcohol (20EO) and acrylic acid |
| to 100 g | water |

Subsequently the hair is treated with the following liquid fixing composition.

| Viscous Fixing Composition | |
|---|---|
| 4.00 g | hydrogen peroxide, 50% aqueous solution |
| 0.50 g | sodium lauryl sulfate |
| 1.00 g | disodium hydrogen phosphate |
| 4.00 g | cetyl stearyl alcohol |
| 0.10 g | salicylic acid |
| 0.30 g | perfume oil |
| to 100 g | water |

The acting time for the fixing composition is 5 minutes. After expiration of this acting time the curlers are unwound and the hair is treated for 15 additional minutes with additional viscous fixing composition. Then it is rinsed with warm water. The hair has beautiful lustrous locks, which are dyed a warm brown shade. Finally the customary styling of the hair with comb and brush follows.

All percentages unless otherwise indicated are percentages by weight.

The disclosure in German Patent Application 101 43 293.3 of Sep. 4, 2001 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a method for simultaneously dyeing and permanent shaping of hair, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method for simultaneously dyeing and permanent shaping of hair, said method comprising the steps of:

a) immediately prior to application on the hair, mixing a hair shaping component (A) containing from 6 to 15 percent by weight of a keratin-reducing substance with a dye component (B) to form a dyeing and shaping composition;

b) treating the hair with the dyeing and shaping composition;

c) then allowing the dyeing and shaping composition to act on the hair for an acting time sufficient for the permanent shaping of the hair amounting to from 3 to 30 minutes;

d) after the allowing of step c), applying to the hair an intervening acidic rinse having a pH of 2 to 6;

e) after the applying of the acidic rinse of step d), treating the hair with a fixing composition;

f) then allowing the fixing composition to act on the hair from 1 to 40 minutes; and subsequently g) rinsing the hair;

wherein the dye component (B) contains at least one oxidative coupler compound and at least one oxidative dyestuff as oxidation dye precursor compounds, and said at least one oxidative dyestuff is selected from the group consisting of 4,5-diamino-1-(2-hydroxyethyl)-1H-pyrazole, 4,5-diamino-1-(1-methylethyl)-1H-pyrazole, 4,5-diamino-1-[(4-methyl-phenyl)methyl]-1H-pyrazole, 4,5-diamino-1-[(4-chlorophenyl)methyl]-1H-pyrazole, 4,5-diamino-1-methylpyrazole, 2-amino-6-methylphenol, 2-amino-5-methyl phenol and p-aminophenol derivatives of formula (i):

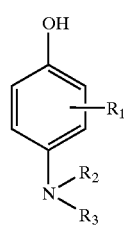

(I)

wherein $R_1$ represents H, —$CH_3$, —$CH_2CH_3$, —$CH_2OH$, —$CH_2CH_2OH$, —$CH_2NH_2$, —$CH_2NHCH_2CH_2OH$ or —$CH_2OCH_3$ and $R_2$ and $R_3$, independently of each other, each represent H, —$CH_3$, —$CH_2CH_3$, —$CH_2OH$, —$CH_2CH_2OH$ or —$CH_2CH_2CH_2OH$, with the proviso that at least one of said $R_1$, $R_2$ and $R_3$ is not H.

2. A method for simultaneously dyeing and permanent shaping of hair, said method comprising the steps of:

a) immediately prior to application on the hair, mixing a hair shaping component (A) containing from 6 to 15 percent by weight of a keratin-reducing substance with a dye component (B) to form a dyeing and shaping composition;

b) treating the hair with the dyeing and shaping composition;

c) then allowing the dyeing and shaping composition to act on the hair for an acting time sufficient for the permanent shaping of the hair amount to from 3 to 30 minutes;

d) after the allowing of step c), applying a pre-fixing composition to the hair;

e) after the applying of the pre-fixing composition of step d), treating the hair with a fixing composition;

f) then allowing the fixing composition to act on the hair from 1 to 40 minutes; and subsequently g) rinsing the hair;

wherein the dye component (B) contains at least one oxidative coupler compound and at least one oxidative dyestuff as oxidation dye precursor compounds, and said at least one oxidative dyestuff is selected from the group consisting of 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 4,5diamino-1-[(4-chlorophenyl)methyl]-1H-pyrazole, 4,5-diamino-1-methylpyrazole, 2-amino-6-methylphenol, 2-amino-5-methyl phenol and p-aminophenol derivatives of formula (I):

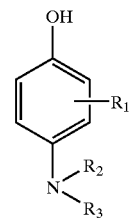

(I)

wherein $R_1$ represents H, —$CH_3$, —$CH_2CH_3$, —$CH_2OH$, —$CH_2CH_2OH$, —$CH_2NH_2$, —$CH_2NHCH_2CH_2OH$ or —$CH_2OCH_3$ and $R_2$ and $R_3$, independently of each other, each represent H, —$CH_3$, —$CH_2CH_3$, —$CH_2OH$, —$CH_2CH_2OH$ or —$CH_2CH_2CH_2OH$, with the proviso that at least one of said $R_1$, $R_2$ and $R_3$ is not H.

3. The method as defined in claim 1 or 2, wherein said at least one oxidative dyestuff is selected from the group consisting of 4,5-diamino-1-(2-hydroxyethyl)-1H-pyrazole, 4,5-diamino-1-(1-methylethyl)-1-H-pyrazole, 4,5-diamino-1-[(4-methylphenyl)methyl]-1H-pyrazole, 4,5-diamino-1-[(4-chlorophenyl)methyl]-1H-pyrazole, 4,5-diamino-1-methylpyrazole, 2-amino-6-methyl-phenol, 2-amino-5-methylphenol, 4-amino-3-methylphenol, 4-methyl-aminophenol, 4-amino-2-(aminomethyl)phenol, 4amino-2-[(2-hydroxyethyl)-amino]-methylphenol and 4-amino-2-(methyoxymethyl)phenol.

4. The method as defined in claim 1 or 2, wherein said at least one oxidative coupler compound is selected from the group consisting of 1,3-diaminobenzene, 2-amino-4-[(2-hydroxyethyl)amino]-anisole, 2,4-diamino-1-fluoro-5-methyl-benzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,4-diamino-1-(2-hydroxyethoxy)-benzene, 3-di[(2-hydroxyethyl)amino]aniline, 3-di[(2-aminoethyl)amino]aniline, 4-amino-1-ethoxy-2-di[(2-hydroxyethyl)amino]-benzene, 3-[(2-hydroxyethyl)-amino]aniline, 1,3-di(2,4-diaminophenoxy)propane, 2,4-dimethoxy-1,3-diamino-benzene, 2,6-bis(2-hydroxyethylaminotoluene, 3-dimethylaminophenol, 5-amino-2-methyl-phenol, 5-amino-4-fluoro-2-methylphenol, 5-amino-4-methoxy-2-methyl-phenol, 5-amino-4-ethoxy-2-methylphenol, 3-amino-2,4-dichlorophenol, 3-dimethylaminophenol, 3-amino-2-chloro-6-methylphenol, 3-aminophenol, 3-[(amidomethyl)-amino]phenol, 5-[(2-hydroxyethyl)amino]-2-methylphenol, 3-[(2-hydroxyethyl)-amino]phenol, 5-amino-2-ethylphenol, 5-[(3-hydroxypropyl)amino]-2-methylphenol, 3-[(2,3-dihydroxypropyl)amino]-2-methylphenol, 3-[(2-hydroxyethyl)-amino]-2-methylphenol, 5-amino-4-chloro-2-methylphenol, methylenedioxyphenol, resorcinol, methylresorcinol and 4-chlororesorcinol.

5. The method as defined in claim 1 or 2, wherein said oxidation dye precursor compounds also include at least one dye member selected from the group consisting of 1,4-diaminobenzene, 1,4-diamino-2-methylbenzene, 1,4-diamino-2,6-dimethylbenzene, 1,4-diamino-2,5-dimethylbenzene, 1,4-diamino-2,3-dimethylbenzene, 1,4-diamino-2-chloro-benzene, 4-di[(2-hydroxyethyl)amino]-aniline, 4-[(2-methoxyethyl)amino]aniline, 1,4-diamino-2-(2-hydroxyethyl)-benzene, 1,3-bis[N-(2-hydroxyethyl)-N-

(4-aminophenyl)]-amino-2-propanol and 2',2-[1,2-ethandiyl-bis(oxy-2,1-ethandiyloxy)]bis-1,4-diaminobenzene.

6. The method as defined in claim 1 or 2, wherein said dye component (B) contains from 0.5 to 30 percent by weight of said oxidation dye precursor compounds.

7. The method as defined in claim 1 or 2, wherein said dyeing and shaping composition contains from 0.1 to 5 percent by weight of said oxidation dye precursor compounds.

8. The method as defined in claim 1 or 2, wherein said dye component (B) and said hair shaping component (A) are mixed to form the dyeing and shaping composition in a weight ratio of 1:1 to 1:10.

9. The method as defined in claim 1 or 2, wherein said keratin-reducing substance is a salt of sulfurous acid or a salt or a derivative of mercapto-carboxylic acid.

10. The method as defined in claim 1 or 2, wherein said keratin-reducing substance is selected from the group consisting of thioglycolic acid, cysteine, thiolactic acid, salts of thioglycolic acid, salts of cysteine and salts of thiolactic acid.

11. The method as defined in claim 1 or 2, wherein the fixing composition is a viscose preparation with a viscosity of 100 to 10,000 mPa·s at 25° C.

12. The method as defined in claim 1 or 2, wherein the fixing composition is a viscose preparation with a viscosity of 300 to 1000 mPa·s at 25° C.

13. The method as defined in claim 1 or 2, wherein the hair is treated with the fixing composition without rinsing the dyeing and shaping composition from the hair.

* * * * *